United States Patent [19]

Kapur

[11] Patent Number: 5,955,458
[45] Date of Patent: Sep. 21, 1999

[54] PENICILLIN GLYCOLATE

[75] Inventor: Jagdish C. Kapur, Delft, Netherlands

[73] Assignee: Gist-Brocades, B.V., Netherlands

[21] Appl. No.: 09/043,949

[22] PCT Filed: Sep. 27, 1996

[86] PCT No.: PCT/EP96/04291

§ 371 Date: Mar. 26, 1998

§ 102(e) Date: Mar. 26, 1998

[87] PCT Pub. No.: WO97/12889

PCT Pub. Date: Apr. 10, 1997

[30] Foreign Application Priority Data

Sep. 29, 1995 [EP] European Pat. Off. ............. 95202626

[51] Int. Cl.$^6$ ................. A01N 43/00; C07D 499/00; C07D 277/60

[52] U.S. Cl. .................. 514/210; 540/304; 548/152
[58] Field of Search ................. 514/210; 540/304; 548/152

[56] References Cited

U.S. PATENT DOCUMENTS 4,863,915 9/1989 Ward ........................................ 514/197

*Primary Examiner*—Mukund J. Shah
*Assistant Examiner*—Tamthom N. Truong
*Attorney, Agent, or Firm*—Bierman, Muserlian and Lucas

[57] ABSTRACT

New solvates of penicillin, in particular amoxycillin glycolate has been provided for together with a simple one-step process to prepare the same.

12 Claims, No Drawings

PENICILLIN GLYCOLATE

This is a 371 application of PCT/EP 96/04291, filed on Sep. 27, 1996.

This invention relates to a glycolate form of a penicillin antibiotic as for instance amoxycillin or ampicillin. In particular this invention relates to a glycolate form of 6-(D-β-amino-p-hydroxyphenylacetamido)-penicillanic acid (amoxycillin) which is substantially free of water, and to a process for the preparation thereof. The solvates of for instance amoxycillin or ampicillin may also be converted into non-toxic, pharmaceutically acceptable salts by a method known per se.

Amoxycillin is known to exist in two forms, namely the crystalline trihydrate form and the mono hydrated amorphous form. The amoxycillin antibiotic is active against Gram-positive and Gram-negative bacteria and is useful as a therapeutic and prophylactic agent against bacterial infections in man including animals.

British patent No. 1286199 describes a process whereby amoxycillin containing a minimum water content of 3–5% can be prepared by drying an alkanolate of amoxycillin trihydrate. However, it has been described that the intermediate alkanolate form is not stable and is subjected to a potency loss after a few days.

European patent No. 0262207 discloses a process for the preparation of crystalline amoxycillin mono-methanolate from amoxycillin trihydrate. A water-free solution of amoxycillin has been prepared by adding molecular sieves 4 Å into a clear solution of amoxycillin trihydrate, obtained by adding triethylamine into a suspension of amoxycillin trihydrate in a mixture of dichloromethane and methanol. Thereafter, the resulting mixture has been treated with acetic acid and, subsequently, by seeding with crystals of amoxycillin methanolate crystalline amoxycillin mono-methanolate has been provided. However, this solvate itself is not unsuspicious for use as medicament.

Now, it has been found that a new glycolate of penicillin antibiotic, especially amoxycillin can surprisingly easily be prepared in good quality from amoxycillin trihydrate and glycole. The new amoxycillin glycolate contains less than 3% of water and is stable, in any case at room temperature.

The present invention provides new penicillin glycolates, in particular amoxycillin glycolate, preferably with a water content of less than 3%. The present invention also provides a process for the preparation of the same by the reaction of penicillin, in particular amoxycillin or ampicillin, and glycol in an organic solvent. Preferably, amoxycillin 1,2-propanediolate has been provided for.

In a preferred embodiment a suspension of amoxycillin has been stirred in a mixture of dichloromethane and 1,2-propanediol for some time and then, after isolating the suspension through filtration, subsequently, thoroughly washed with dichloromethane and dried. Formation of a gelatinous type of product has not been observed. The amoxycillin 1,2-propanediolate may contain about 0.5 mol of 1,2-propanediol.

The present invention also provides a pharmaceutical composition which comprises penicillin, in particular amoxycillin glycolate or ampicillin glycolate and a pharmaceutically acceptable carrier. The compositions of the invention include those in a form adapted for oral, topical or parenteral use and may be used for the treatment of infections in mammals including humans.

The penicillin, in particular amoxycillin glycolate or ampicillin glycolate may be the sole therapeutic agent in the composition of the invention or a combination with other antibiotics or with a β-lactamase inhibitor as for instance clavulanic acid preferably in its potassium clavulanate form, or sulbactam, may be employed.

The following example illustrates the process according to the invention without, however, being considered to be restricted thereto.

EXAMPLE

Preparation of amoxycillin 1,2-propanediolate

Dichloromethane (63 ml; methanol-free) was added to amoxycillin trihydrate (3.5 g; purity by HPLC 86%; water 12.9%) with stirring at room temperature and, then, followed by the addition of 1,2-propanediol (22 ml). The reaction mixture was further stirred for about 20 min at the same temperature. The product was filtered and, then, washed on the filter with dichloromethane (100 ml). Thereafter, the product was suspended in dichloromethane (80 ml) and stirred for about 20 min at room temperature. The resulting suspension was filtered, washed on the filter with dichloromethane (100 ml) and, then, dried under vacuum overnight.

Results of the analysis:

HPLC: 88.5% of amoxycillin, as calculated as free acid

Water (KF): 2.1%

NMR: Molecular ratio: amoxycillin/1,2-propanediol=ca. 65/35, indicating the presence of about ½ mole of 1,2-propanediol compared to amoxycillin 1 mole IR (in nujol mul): 1773 (beta-lactam

I claim:

1. Penicillin glycolate and a pharmaceutically acceptable salt thereof.

2. Penicillin glycolate according to claim 1 where the penicillin glycolate is amoxycillin glycolate.

3. Amoxycillin glycolate according to claim 2 with a water content of less than 3%.

4. Amoxycillin glycolate according to claim 2, consisting essentially of glycolate and amoxycillin in a ratio of 1:2.

5. Amoxycillin glycolate according to claim 1, wherein the glycolate is 1,2-propanediolate.

6. A process for the preparation of penicillin glycolate as defined in claim 1, characterized by the reaction of penicillin hydrate and glycol in an organic solvent and optional conversion into a pharmaceutically acceptable salt.

7. A process for the preparation of amoxycillin glycolate as defined in claim 2, characterized by the reaction of amoxycillin trihydrate and glycol in an organic solvent and optional conversion into a pharmaceutically acceptable salt.

8. A process according to claim 6, characterized in that the organic solvent used is dichloromethane.

9. A pharmaceutical composition comprising an effective amount of penicillin glycolate as defined in claim 1.

10. A pharmaceutical composition according to claim 9 comprising an effective amount of penicillin glycolate and clavulanate or sulbactam.

11. A pharmaceutical composition according to claim 9 comprising an effective amount of amoxycillin glycolate and clavulanate.

12. A pharmaceutical composition according to claim 9 comprising an effective amount of ampicillin glycolate and sulbactam.

* * * * *